United States Patent
Shiraishi et al.

(10) Patent No.: US 11,406,357 B2
(45) Date of Patent: Aug. 9, 2022

(54) CRADLE APPARATUS

(71) Applicant: Konica Minolta, Inc., Tokyo (JP)

(72) Inventors: Takahiko Shiraishi, Tokyo (JP); Tatsushi Chihara, Tokyo (JP); Shinya Noguchi, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 447 days.

(21) Appl. No.: 16/195,291

(22) Filed: Nov. 19, 2018

(65) Prior Publication Data

US 2019/0200958 A1 Jul. 4, 2019

(30) Foreign Application Priority Data

Dec. 28, 2017 (JP) .............................. JP2017-253718

(51) Int. Cl.
  *A61B 8/00* (2006.01)
  *F16M 11/00* (2006.01)
(52) U.S. Cl.
  CPC .......... *A61B 8/4433* (2013.01); *A61B 8/4209* (2013.01); *A61B 8/4405* (2013.01);
  (Continued)
(58) Field of Classification Search
  CPC ...... F16M 11/00; F16M 11/04; F16M 11/041; F16M 2200/024; A61B 8/4209; A61B 8/56; A61B 8/4405; A61B 8/4433; A61B 8/4427; G06F 1/1632
  See application file for complete search history.

(56) References Cited

U.S. PATENT DOCUMENTS 8,767,396 B2 * 7/2014 Shindo .................. H05K 5/023
  361/679.59
10,019,034 B2 * 7/2018 Barnett ................. G06F 3/0338
  (Continued)

FOREIGN PATENT DOCUMENTS

CN   1421088 A   5/2003
CN   2872644 Y  *  2/2007
  (Continued)

OTHER PUBLICATIONS

CNIPA, Office Action for the corresponding Chinese Patent Application No. 201811589547.4, dated Jun. 17, 2020, with English translation.
(Continued)

*Primary Examiner* — Amanda Lauritzen Moher
*Assistant Examiner* — Sean V Blinder
(74) *Attorney, Agent, or Firm* — Lucas & Mercanti, LLP (57) ABSTRACT

A cradle apparatus configured to detachably support an ultrasound diagnostic apparatus, the cradle apparatus including: a base portion configured to support a bottom portion of the ultrasound diagnostic apparatus; a back supporting portion extending from the base portion along an attaching/detaching direction of the ultrasound diagnostic apparatus, the back supporting portion being configured to support a back portion of the ultrasound diagnostic apparatus on a side opposite to a front portion of the ultrasound diagnostic apparatus, the front portion being provided with a display device; and a guide disposed in the back supporting portion and configured to be fitted with a rail provided in the back portion of the ultrasound diagnostic apparatus so as to allow the ultrasound diagnostic apparatus to slide along the attaching/detaching direction.

13 Claims, 10 Drawing Sheets

(52) U.S. Cl.
CPC .......... *A61B 8/4411* (2013.01); *A61B 8/4427* (2013.01); *A61B 8/4444* (2013.01); *A61B 8/56* (2013.01); *F16M 11/00* (2013.01)

(56) References Cited

U.S. PATENT DOCUMENTS

| | | | | |
|---|---|---|---|---|
| 2002/0143256 A1* | 10/2002 | Wing | .................... | G06F 1/1632 600/459 |
| 2009/0270727 A1* | 10/2009 | Zhao | .................... | A61B 8/4433 600/437 |
| 2011/0077557 A1* | 3/2011 | Wing | ................ | B01D 19/0042 601/2 |
| 2015/0190114 A1* | 7/2015 | Ninomiya | ............... | G06F 1/166 600/437 |

FOREIGN PATENT DOCUMENTS

| | | | |
|---|---|---|---|
| CN | 2872644 | Y | 2/2007 |
| CN | 101271349 | A | 9/2008 |
| CN | 101569537 | A | 11/2009 |
| CN | 101271349 | B * | 5/2010 |
| JP | H11-155005 | A | 6/1999 |
| JP | H11-177670 | A | 7/1999 |
| JP | 2009-200799 | A | 9/2009 |
| JP | 2015-008796 | A | 1/2015 |
| JP | 3196455 | U | 3/2015 |
| JP | 2015-515312 | A | 5/2015 |

OTHER PUBLICATIONS

JPO, Office Action for the corresponding Japanese Patent Application No. 2017-253718, dated Jul. 13, 2021, with English translation.

JPO, Office Action for the corresponding Japanese Patent Application No. 2017-253718, dated Dec. 21, 2021, with English translation.

JPO, Office Action for the corresponding Japanese Patent Application No. 2017-253718, dated May 24, 2022, with English translation.

* cited by examiner

CRADLE APPARATUS

CROSS REFERENCE TO RELATED APPLICATIONS

The entire disclosure of Japanese Patent Application No. 2017-253718 filed on Dec. 28, 2017 is incorporated herein by reference in its entirety.

BACKGROUND

Technological Field

The present invention relates to a cradle apparatus.

Description of Related Art

Conventionally, an ultrasound diagnostic apparatus is known in which ultrasound waves are transmitted to and/or received from a subject a such as a living body with an ultrasound probe, an ultrasound image data is generated based on a signal obtained from the received ultrasound waves, and an ultrasound image based on the data is displayed on an image display device. Ultrasound diagnosis using the above-mentioned apparatus can obtain the condition of a subject such as heartbeat and fetal movement with a simple operation in real time, and is non-invasive and highly safe, and therefore, can be repeatedly implemented. In addition, in recent years, small-sized mobile ultrasound diagnostic apparatuses have been practically used, providing high mobility or the like (e.g. Japanese Patent Application Laid-Open No. 2015-008796).

SUMMARY

However, a cradle apparatus for detachably supporting a mobile ultrasound diagnostic apparatus for a case that, for example, the ultrasound diagnostic apparatus is required to be used in a fixed manner in a hospital room or the like has not been proposed.

An object of the present invention is to provide a cradle apparatus which readily and detachably supports an ultrasound diagnostic apparatus.

To achieve the abovementioned object, a cradle apparatus reflecting one aspect of the present invention is configured to detachably support an ultrasound diagnostic apparatus, the cradle apparatus including: a base portion configured to support a bottom portion of the ultrasound diagnostic apparatus; a back supporting portion extending from the base portion along an attaching/detaching direction of the ultrasound diagnostic apparatus, the back supporting portion being configured to support a back portion of the ultrasound diagnostic apparatus on a side opposite to a front portion of the ultrasound diagnostic apparatus, the front portion being provided with a display device; and a guide disposed in the back supporting portion and configured to be fitted with a rail provided in the back portion of the ultrasound diagnostic apparatus so as to allow the ultrasound diagnostic apparatus to slide along the attaching/detaching direction.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

An embodiment of the present invention is described below with reference to the accompanying drawings.

Figure 1:
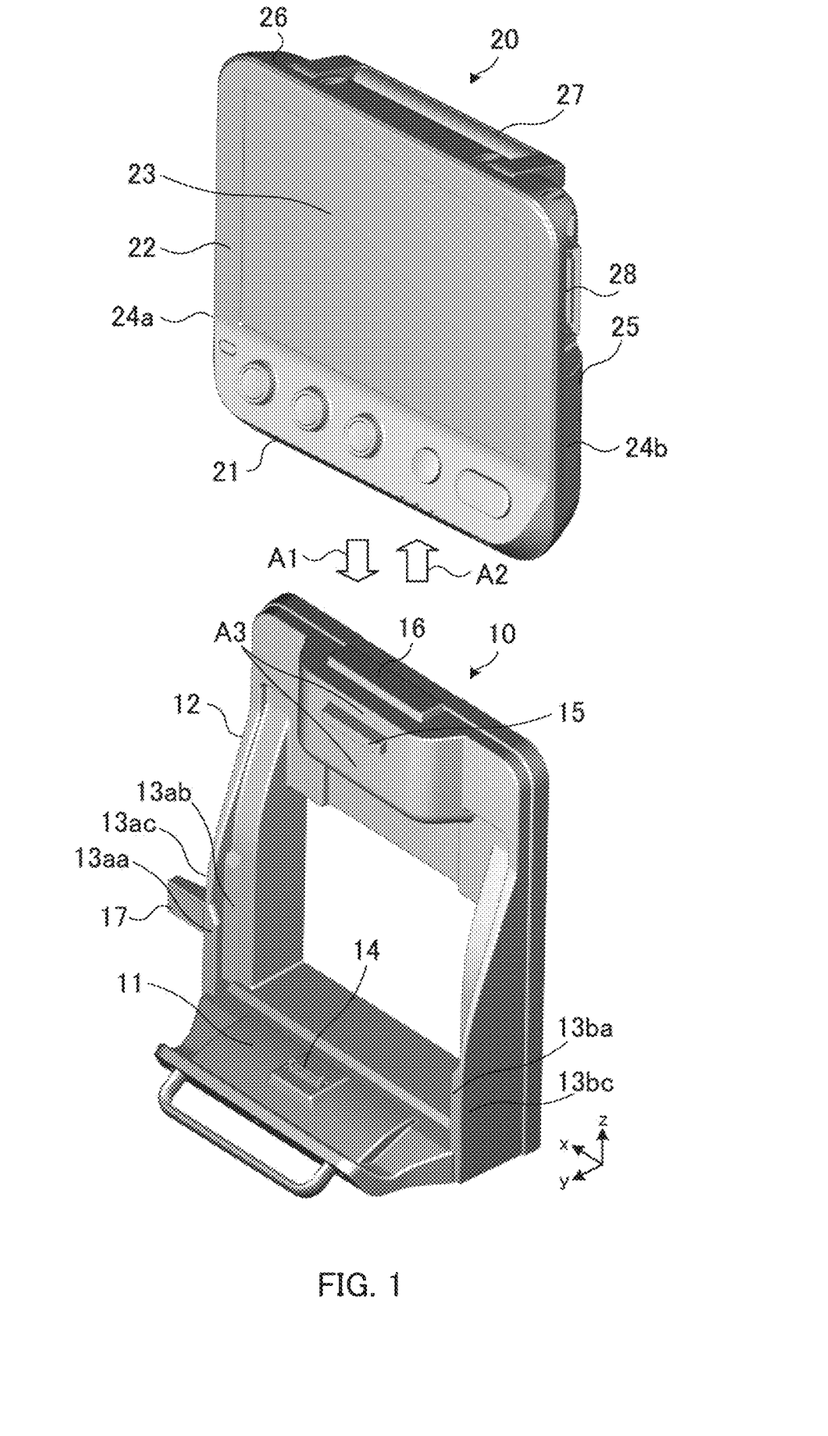
FIG. 1 is a perspective view illustrating a cradle apparatus according to an embodiment of the present invention.

FIG. 1 is a perspective view illustrating cradle apparatus 10 according to the embodiment of the present invention. FIG. 1 also illustrates mobile ultrasound diagnostic apparatus 20 which is attached to or detached from cradle apparatus 10. In the following description, an orthogonal coordinate system with x, y, z axes are set to cradle apparatus 10 and ultrasound diagnostic apparatus 20 as illustrated in FIG. 1. In addition, in FIG. 1, +y axis direction corresponds to the frontward direction with respect to cradle apparatus 10 and ultrasound diagnostic apparatus 20, and −y axis direction corresponds to the rearward direction with respect to cradle apparatus 10 and ultrasound diagnostic apparatus 20.

Ultrasound diagnostic apparatus 20 is mounted into cradle apparatus 10 from the upper side of cradle apparatus 10. For example, ultrasound diagnostic apparatus 20 is mounted into cradle apparatus 10 by being pushed toward cradle apparatus 10 in the direction of arrow A illustrated in FIG. 1 (−z axis direction).

Figure 2:
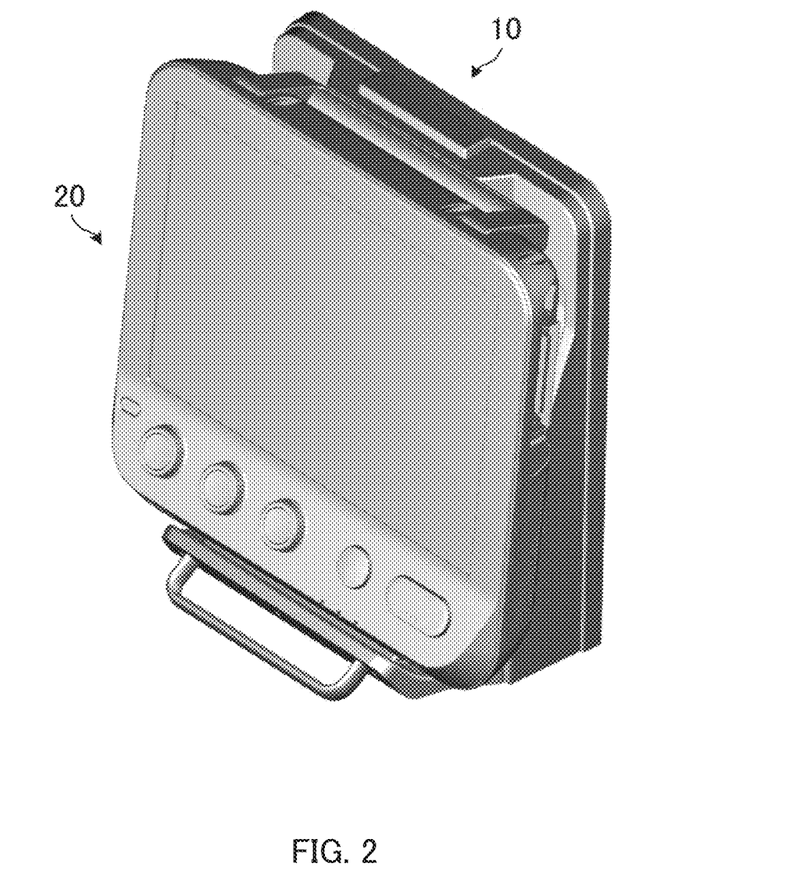
FIG. 2 is a perspective view illustrating a state that an ultrasound diagnostic apparatus is mounted in the cradle apparatus.

FIG. 2 is a perspective view illustrating a state that ultrasound diagnostic apparatus 20 is mounted in cradle apparatus 10. In FIG. 2, the components same as those of FIG. 1 are illustrated with the same reference numerals. As described above, ultrasound diagnostic apparatus 20 is mounted in cradle apparatus 10 as illustrated in FIG. 2 by being pushed toward cradle apparatus 10 from the upper side of cradle apparatus 10 (the state illustrated in FIG. 1).

The description is returned to FIG. 1. Ultrasound diagnostic apparatus 20 mounted in cradle apparatus 10 is dismounted from cradle apparatus 10 when pulled up from cradle apparatus 10. For example, ultrasound diagnostic apparatus 20 mounted in cradle apparatus 10 is dismounted from cradle apparatus 10 when pulled up in the direction of arrow A2 illustrated in FIG. 1 (+z-axis direction).

Cradle apparatus 10 is fixed to a cart, for example. When ultrasound diagnostic apparatus 20 is mounted in cradle apparatus 10 fixed to a cart, ultrasound diagnostic apparatus 20 can be moved with the cart. In addition, ultrasound diagnostic apparatus 20 can be freely carried when dismounted from cradle apparatus 10 fixed to a cart.

Figure 3:
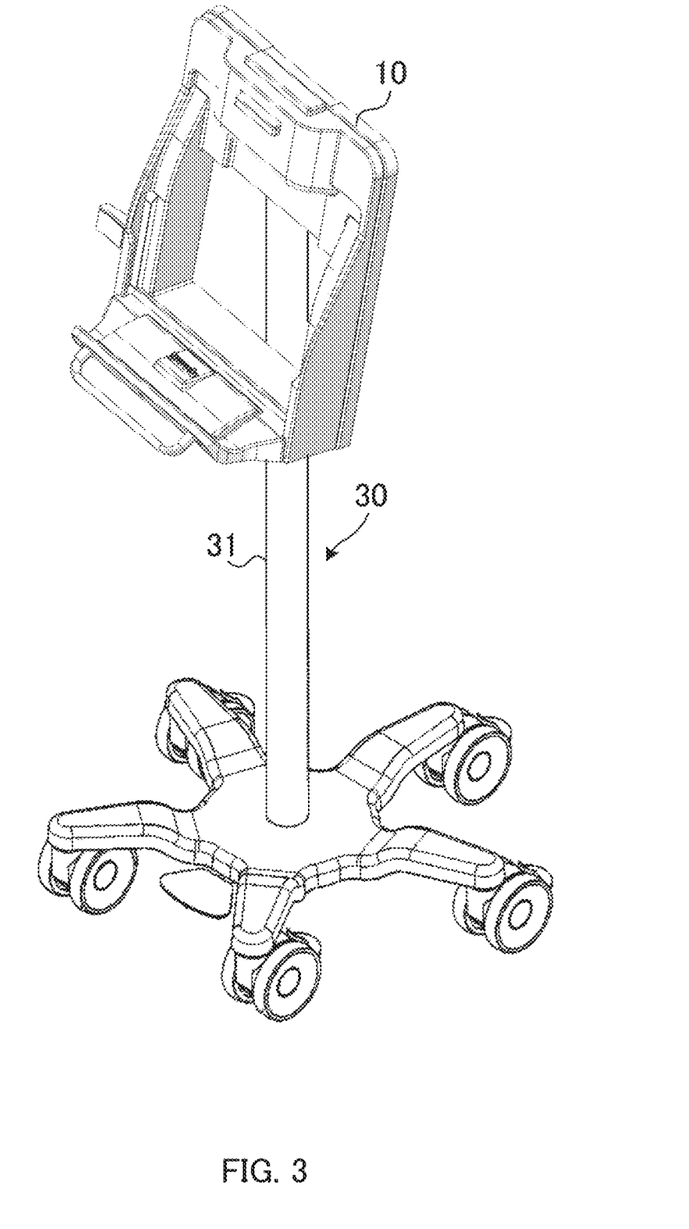
FIG. 3 illustrates the cradle apparatus fixed to a cart.

FIG. 3 illustrates cradle apparatus 10 fixed to cart 30. FIG. 3 illustrates cradle apparatus 10 illustrated in FIG. 1 and cart 30 provided with a caster.

As illustrated in FIG. 3, cart 30 includes arm 31. Cradle apparatus 10 is fixed to the top end of arm 31. For example, cradle apparatus 10 is fixed to the top end of arm 31 with a screw. With this configuration, ultrasound diagnostic apparatus 20 can be readily moved by moving cart 30 provided with a caster.

It is to be noted that cradle apparatus 10 may be fixed to a part other than cart 30. For example, cradle apparatus 10 may be fixed to a wall or a shelf of a hospital room or the like. With this configuration, when mounted in cradle apparatus 10 fixed to a wall or a shelf of a hospital room or the like, ultrasound diagnostic apparatus 20 can be used in a fixed manner in a hospital room.

The description is returned to FIG. 1. Cradle apparatus 10 includes base portion 11, back supporting portion 12, guides 13aa, 13ab, 13ac, 13ba and 13bc, connector 14 (second connector), protrusion 15, button 16, and panel 17.

Base portion 11 supports the bottom portion (bottom surface) of ultrasound diagnostic apparatus 20 mounted in cradle apparatus 10. The surface of base portion 11 which makes contact with the bottom portion of ultrasound diagnostic apparatus 20 has a shape which matches the bottom surface of ultrasound diagnostic apparatus 20 so as to stably support ultrasound diagnostic apparatus 20 mounted in cradle apparatus 10.

Back supporting portion 12 extends along the attaching/detaching direction (z-axis direction) of ultrasound diagnostic apparatus 20 from base portion 11. Back supporting portion 12 supports the back portion (back surface) of ultrasound diagnostic apparatus 20 mounted in cradle apparatus 10.

Guides 13aa, 13ab and 13ac are formed on the left side of back supporting portion 12 as viewed from the front of cradle apparatus 10. Each of guides 13aa, 13ab and 13ac has a plate shape, and extends along the attaching/detaching direction (z-axis direction) of ultrasound diagnostic apparatus 20.

Guides 13aa and 13ab face each other with a space (see, e.g., dotted line A31 of FIG. 8) defined therebetween. A variable stand (see variable stand 43 of FIG. 4 and FIG. 5) of ultrasound diagnostic apparatus 20 described later is inserted to the space defined between guides 13aa and 13ab.

Guide 13ac couples guides 13aa and 13ab facing each other. Guide 13ac couples guides 13aa and 13ab on the left side of guides 13aa and 13ab as viewed from the front of cradle apparatus 10.

Guide 13ba is provided on the right side of back supporting portion 12 as viewed from the front of cradle apparatus 10. In FIG. 1, back supporting portion 12 is provided with a guide which faces guide 13ba although not shown in the drawing (see guide 13bb of FIG. 8 and FIG. 9). Each of guide 13ba and the guide facing guide 13ba has a plate shape, and extends along the attaching/detaching direction of ultrasound diagnostic apparatus 20. The variable stand of ultrasound diagnostic apparatus 20 described later is inserted to the space defined between guide 13ba and the guide facing guide 13ba (see, e.g., dotted line A32 of FIG. 8).

Figure 8:
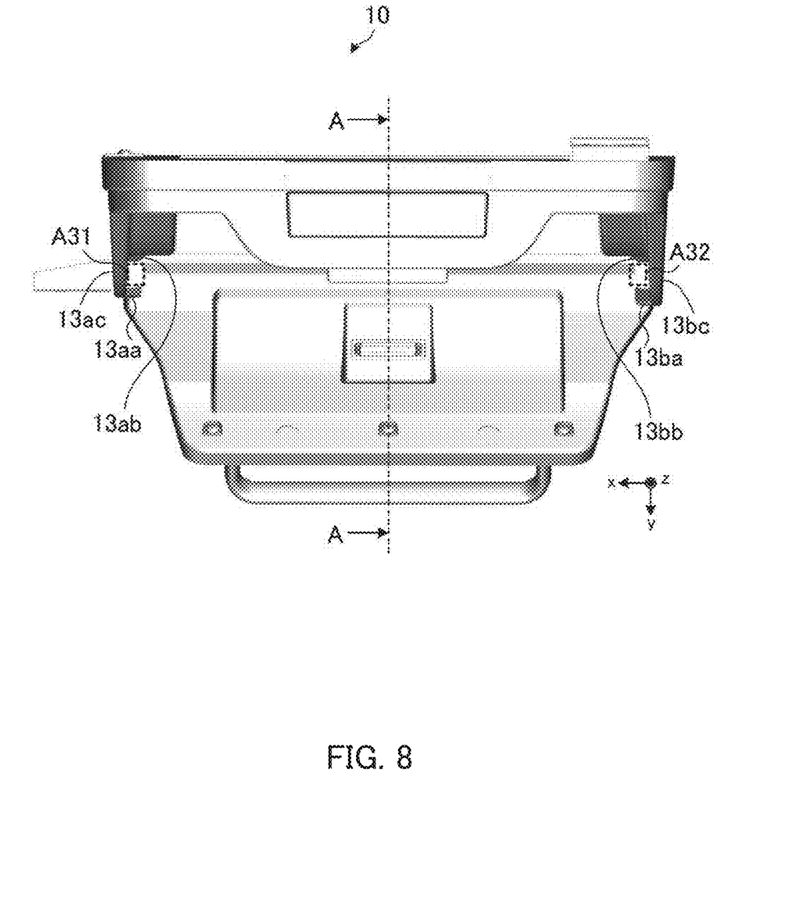
FIG. 8 is a top view of the cradle apparatus.
Figure 9:
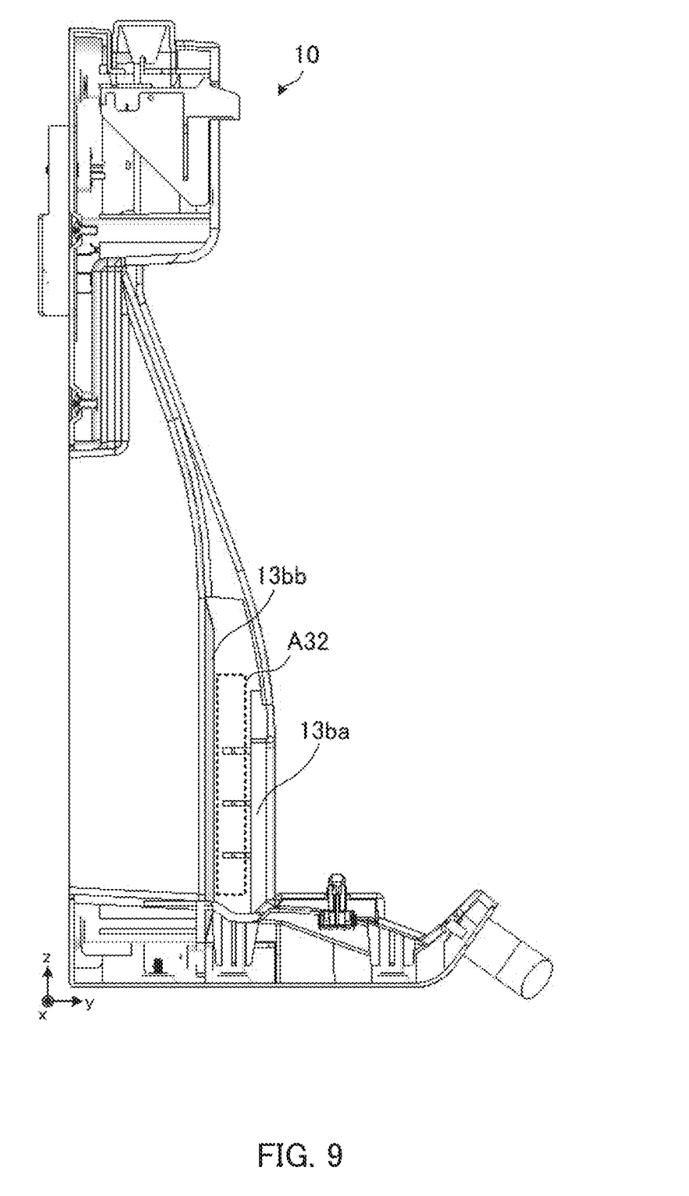
FIG. 9 is a sectional view taken along line A-A of FIG. 8.

Guide 13bc couples guide 13ba and the guide facing guide 13ba (see guide 13bb of FIG. 8 and FIG. 9). Guide 13bc has a plate shape, and extends along the attaching/detaching direction of ultrasound diagnostic apparatus 20. On the right side of guide 13ba and the guide facing guide 13ba as viewed from the front of cradle apparatus 10, guide 13bc couples guide 13ba and the guide facing guide 13ba.

Connector 14 is provided in base portion 11. When ultrasound diagnostic apparatus 20 is mounted in cradle apparatus 10, connector 14 is fitted with the connector provided in the bottom portion of ultrasound diagnostic apparatus 20.

Protrusion 15 protrudes frontward from back supporting portion 12 of cradle apparatus 10. When button 16 is pressed down, protrusion 15, which is coupled with button 16, is moved rearward of cradle apparatus 10, and pressed into back supporting portion 12. It is to be noted that, when ultrasound diagnostic apparatus 20 is mounted in cradle apparatus 10, a part of back supporting portion 12 in a region around protrusion 15 (e.g. the portion indicated by arrow A3) makes contact with the back portion of ultrasound diagnostic apparatus 20 and supports ultrasound diagnostic apparatus 20.

Protrusion 15 has a substantially cuboid shape. When ultrasound diagnostic apparatus 20 is mounted in cradle apparatus 10, protrusion 15 is fitted with a recess provided in the back portion of ultrasound diagnostic apparatus 20 (see recess 41 of FIG. 4). When button 16 is pressed down, fitting of protrusion 15 with the recess provided in the back portion of ultrasound diagnostic apparatus 20 is released. That is, when button 16 is not pressed down, ultrasound diagnostic apparatus 20 mounted in cradle apparatus 10 cannot be dismounted from ultrasound diagnostic apparatus 20 (ultrasound diagnostic apparatus 20 cannot be pulled up in arrow A2 direction).

Button 16 is provided in an upper portion (top surface) of back supporting portion 12. Button 16, which is coupled with protrusion 15, pushes protrusion 15 into back supporting portion 12 when pressed down in the −z axis direction.

As viewed from the front of cradle apparatus 10, panel 17 is formed on the left side of back supporting portion 12. Panel 17 has a plate shape. Panel 17 is formed such that a power connector (see power connector 42 of FIG. 4) provided in the back portion of ultrasound diagnostic apparatus 20 is hidden when ultrasound diagnostic apparatus 20 is mounted in cradle apparatus 10. That is, when ultrasound diagnostic apparatus 20 is mounted in cradle apparatus 10, panel 17 does not allow the power cable to be connected with ultrasound diagnostic apparatus 20. It is to be noted that, the position of panel 17 is not limited to the position illustrated in the drawing. The position where panel 17 is provided in back supporting portion 12 is not limited as long as the position corresponds to the position of power connector (position where the power connector is hidden) of the back portion of ultrasound diagnostic apparatus 20 mounted in cradle apparatus 10.

Ultrasound diagnostic apparatus 20 includes bottom portion 21, front portion 22, display device 23, side portions 24a and 24b, back portion 25, upper portion 26, handle 27, and connector 28. Ultrasound diagnostic apparatus 20 has a substantially cuboid shape.

Bottom portion 21 is the bottom surface of ultrasound diagnostic apparatus 20. Although not illustrated in FIG. 1, bottom portion 21 is provided with a connector (see connector 51 of FIG. 6). The connector provided in bottom portion 21 is fitted with connector 14 of cradle apparatus 10 when ultrasound diagnostic apparatus 20 is mounted in cradle apparatus 10.

Front portion 22 is the front surface of ultrasound diagnostic apparatus 20. Front portion 22 is provided with display device 23. Display device 23 is a display device of a LCD (Liquid Crystal Display) or an OLED (Organic Light-Emitting diode). A touch panel is provided in the top surface of display device 23.

Side portions 24a and 24b are the side surfaces of ultrasound diagnostic apparatus 20. One of or both of side portions 24a and 24b are provided with connector 28 to which a cable of an ultrasound probe is connected. In the example illustrated in FIG. 1, connector 28 is provided in side portion 24b.

Back portion 25 is the back surface of ultrasound diagnostic apparatus 20. Upper portion 26 is the top surface of ultrasound diagnostic apparatus 20. Upper portion 26 is provided with handle 27. Handle 27 is put into a state that handle 27 is laid on upper portion 26 and a state that handle 27 is raised from upper portion 26. In FIG. 1, handle 27 is laid.

The cable of the ultrasound probe is connected to connector 28. A signal of the ultrasound probe connected with connector 28 is input to connector 28. In response to an input signal, ultrasound diagnostic apparatus 20 generates ultrasound image data, and displays an ultrasound image based on the ultrasound image data on display device 23.

Figure 4:
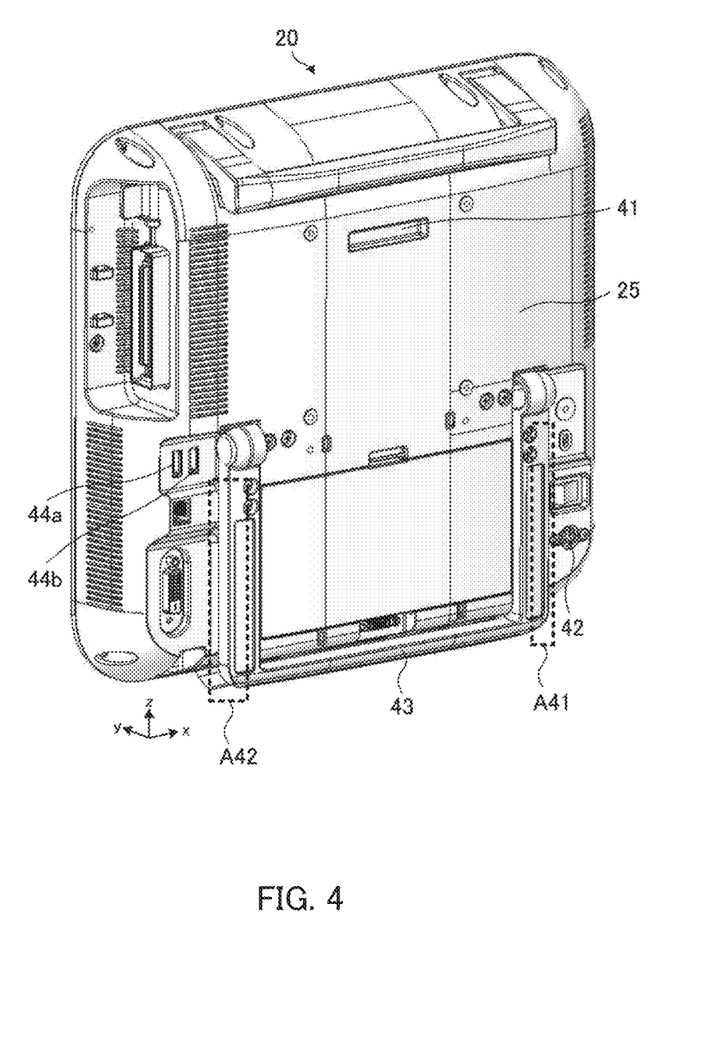
FIG. 4 is a rear perspective view of the ultrasound diagnostic apparatus.

FIG. 4 is a rear perspective view of ultrasound diagnostic apparatus 20. As illustrated in FIG. 4, back portion 25 of ultrasound diagnostic apparatus 20 includes recess 41, power connector 42, variable stand 43, and USB (Universal Serial Bus) connectors 44a and 44b.

Recess 41 is depressed inward (inside) of ultrasound diagnostic apparatus 20. Recess 41 has a shape which is fitted with protrusion 15 of cradle apparatus 10 when ultrasound diagnostic apparatus 20 is mounted in cradle apparatus 10. For example, recess 41 has a substantially cuboid shape.

When ultrasound diagnostic apparatus 20 is mounted in cradle apparatus 10, protrusion 15 of cradle apparatus 10 is engaged with recess 41. With this configuration, ultrasound diagnostic apparatus 20 is not allowed to be dismounted from cradle apparatus 10. Ultrasound diagnostic apparatus 20 can be dismounted from cradle apparatus 10 by pressing down button 16 of cradle apparatus 10, and by pulling up ultrasound diagnostic apparatus 20 by gripping handle 27 of ultrasound diagnostic apparatus 20.

A connector of a power cable is connected to power connector 42. When the connector of the power cable is connected with power connector 42, external power is supplied to ultrasound diagnostic apparatus 20.

When ultrasound diagnostic apparatus 20 is mounted in cradle apparatus 10, panel 17 of cradle apparatus 10 does not allow power connector 42 to be connected with the connector of the power cable. That is, when ultrasound diagnostic apparatus 20 is mounted in cradle apparatus 10, power connector 42 is hidden by panel 17 of cradle apparatus 10. As described later, when ultrasound diagnostic apparatus 20 is mounted in cradle apparatus 10, external power is supplied to ultrasound diagnostic apparatus 20 from connector 14 of cradle apparatus 10.

Variable stand 43 is a stand for putting ultrasound diagnostic apparatus 20 up on a table, for example. Variable stand 43 is housed in back portion 25 or raised from back portion 25. FIG. 4 illustrates a state that variable stand 43 is housed.

Ultrasound diagnostic apparatus 20 is mounted in cradle apparatus 10 by housing variable stand 43. That is, when variable stand 43 is in the state illustrated in FIG. 4, ultrasound diagnostic apparatus 20 can be mounted in cradle apparatus 10.

Figure 5:
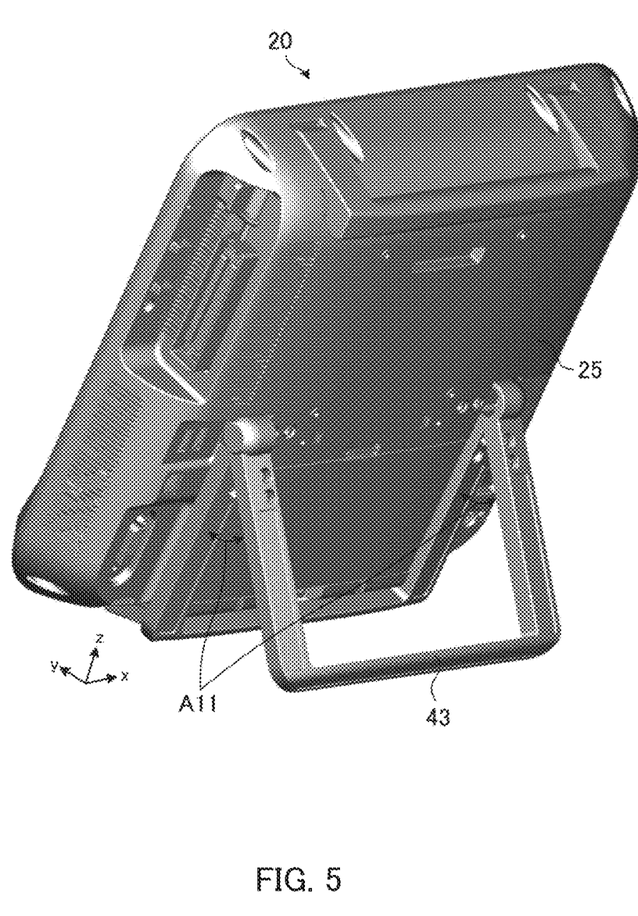
FIG. 5 illustrates a standing state of a variable stand of the ultrasound diagnostic apparatus.

FIG. 5 illustrates a standing state of variable stand 43 of ultrasound diagnostic apparatus 20. In FIG. 5, the components same as those of FIG. 4 are illustrated with the same reference numerals. As illustrated in FIG. 5, variable stand 43 can be raised from back portion 25 of ultrasound diagnostic apparatus 20. The raising angle of variable stand 43 can be changed. For example, the angle of arrow A11 illustrated in FIG. 5 can be changed.

With this configuration, ultrasound diagnostic apparatus 20 can be used in a standing state on a table. In addition, by changing the angle of variable stand 43, the angle of display device 23 to the operator of ultrasound diagnostic apparatus 20 can be changed.

The description is returned to FIG. 4. A connector of a USB cable is connected to USB connectors 44a and 44b. When a connector of a USB cable is connected with USB connectors 44a and 44b, ultrasound diagnostic apparatus 20 can communicate with an external apparatus.

Examples of the external apparatus include a keyboard and a foot switch. The foot switch is, for example, a switch for temporarily stopping the screen of display device 23 of ultrasound diagnostic apparatus 20. For example, the operator of ultrasound diagnostic apparatus 20 can temporarily stop the screen of display device 23 of ultrasound diagnostic apparatus 20 by pressing the foot switch.

Figure 6:
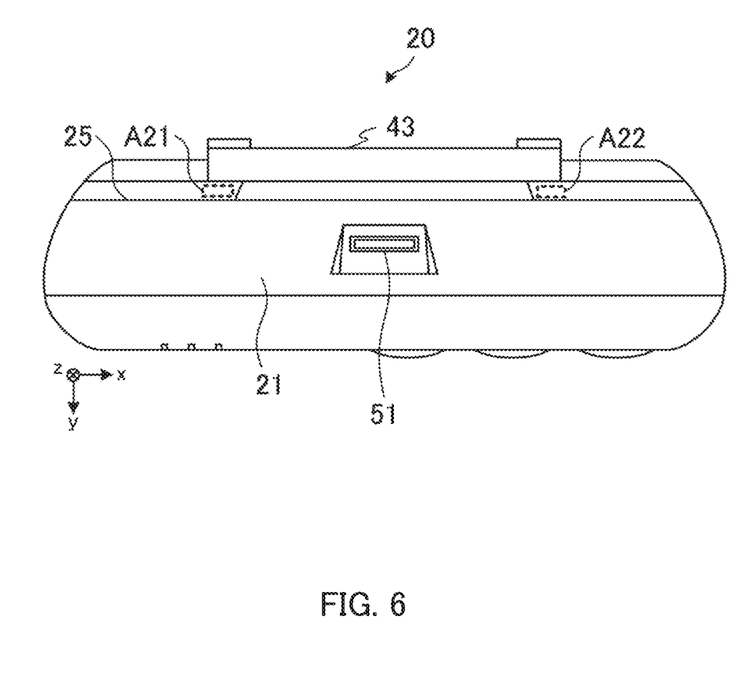
FIG. 6 is a bottom view of the ultrasound diagnostic apparatus.

FIG. 6 is a bottom view of ultrasound diagnostic apparatus 20. In FIG. 6, the components same as those of FIG. 1 and FIG. 4 are illustrated with the same reference numerals. As illustrated in FIG. 6, connector 51 (first connector) is provided in bottom portion 21 of ultrasound diagnostic apparatus 20. When ultrasound diagnostic apparatus 20 is mounted in cradle apparatus 10, connector 51 is connected with connector 14 of cradle apparatus 10.

A space (gap) is defined between housed variable stand 43 and the surface of back portion 25. For example, as indicated with dotted lines A21 and A22 in FIG. 6, a space is defined between housed variable stand 43 and the surface of back portion 25. This space extends along the attaching/detaching direction (z-axis direction) of ultrasound diagnostic apparatus 20 as described below with reference to FIG. 7.

Figure 7:
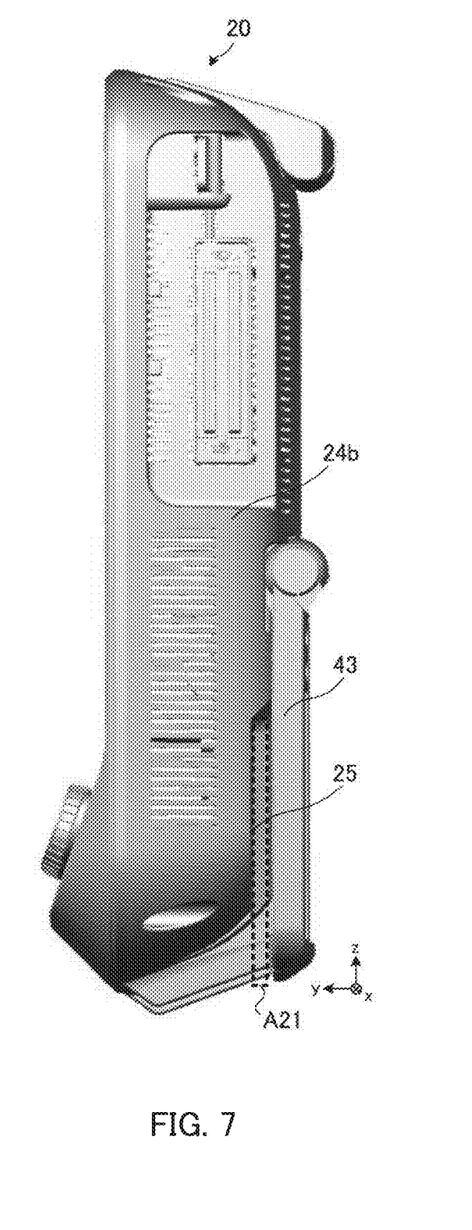
FIG. 7 is a side view of the ultrasound diagnostic apparatus.

FIG. 7 is a side view of ultrasound diagnostic apparatus 20. In FIG. 7, the components same as those of FIGS. 1, 4, and 6 are illustrated with the same reference numerals. As indicated with dotted line A21 (see also dotted line A21 of FIG. 6) in FIG. 7, the space between housed variable stand 43 and the surface of back portion 25 extends along the z-axis direction. Also, the space indicated with dotted line A22 in FIG. 6 extends along the z-axis direction as with dotted line A21 in FIG. 7. When ultrasound diagnostic apparatus 20 is mounted in cradle apparatus 10, guides 13aa and 13ba of cradle apparatus 10 are inserted to the space indicated with dotted lines A21 and A22.

FIG. 8 is a top view of cradle apparatus 10. In FIG. 8, the components same as those of FIG. 1 are illustrated with the same reference numerals.

As described with reference to FIG. 1, guides 13aa and 13ab face each other, and define a space. For example, as indicated with dotted line A31 in FIG. 8, a space is defined between guides 13aa and 13ab. Likewise, guides 13ba and 13bb face each other and define a space. For example, as indicated with dotted line A32 in FIG. 8, a space is defined between guides 13ba and 13bb.

FIG. 9 is a sectional view taken along line A-A of FIG. 8. In FIG. 9, the components same as those of FIG. 8 are illustrated with the same reference numerals. Guides 13ba and 13bb extend along the attaching/detaching direction (z-axis direction) of ultrasound diagnostic apparatus 20.

Accordingly, the space defined between guides 13*ba* and 13*bb* also extends along the z-axis direction as indicated with dotted line A32 (see also dotted line A32 of FIG. 8). The space indicated with dotted line A31 in FIG. 8 also extends along the z-axis direction as with dotted line A32 indicated in FIG. 9.

When ultrasound diagnostic apparatus 20 is mounted in cradle apparatus 10, the portion extending along the attaching/detaching direction (z-axis direction) of variable stand 43 of ultrasound diagnostic apparatus 20 is inserted to the space as indicated with dotted lines A31 and A32 in FIG. 8. For example, the portion indicated with dotted line A41 in FIG. 4 is inserted to the space indicated with dotted line A31 in FIG. 8, and the portion indicated with dotted line A42 in FIG. 4 is inserted to the space indicated with dotted line A32 in FIG. 8.

In addition, when ultrasound diagnostic apparatus 20 is mounted in cradle apparatus 10, guide 13*aa* of cradle apparatus 10 illustrated in FIG. 8 is inserted to the space indicated with dotted line A22 in FIG. 6, and guide 13*bb* of cradle apparatus 10 illustrated in FIG. 8 is inserted to the space indicated with dotted line A21 in FIG. 6.

That is, the portion of variable stand 43 extending along the attaching/detaching direction are inserted between guides 13*aa* and 13*ab*, and between guides 13*ba* and 13*bb*. In other words, the portion of variable stand 43 extending along the attaching/detaching direction serves a function of a rail, and slides along the attaching/detaching direction between guides 13*ba* and 13*bb* and between guides 13*aa* and 13*ab* extending along the attaching/detaching direction.

It is to be noted that guides 13*aa*, 13*ab*, 13*ba* and 13*bb* limit (restrict) the movement in the y-axis direction of ultrasound diagnostic apparatus 20 mounted in cradle apparatus 10. Guides 13*ac* and 13*bc* limit the movement in the x-axis direction of ultrasound diagnostic apparatus 20 mounted in cradle apparatus 10.

Figure 10:
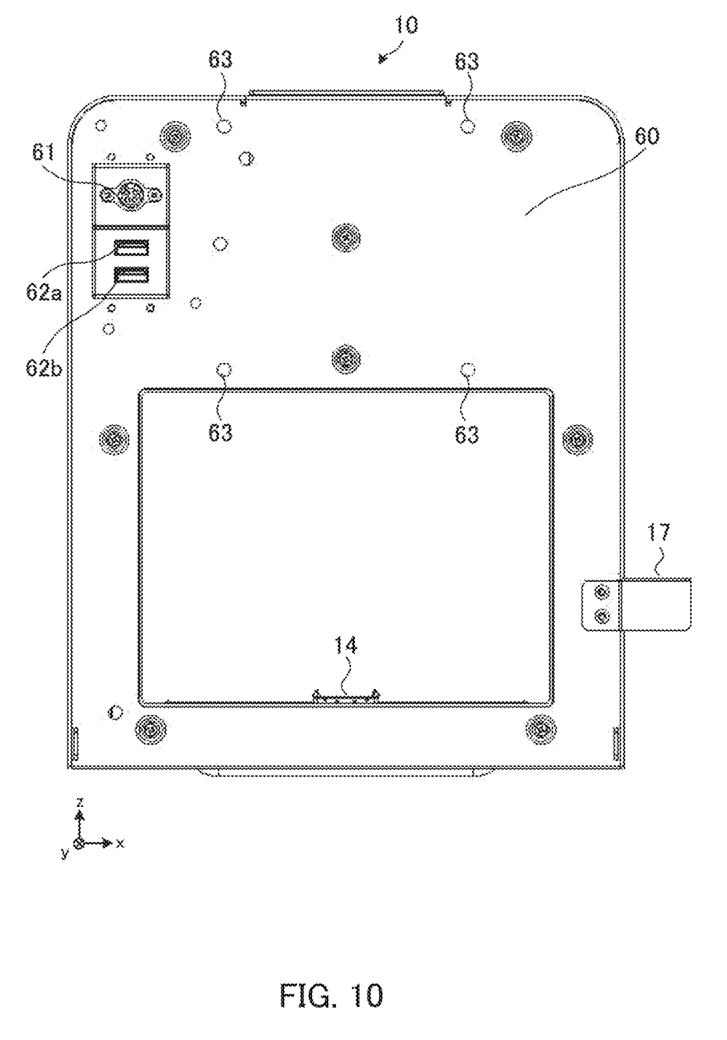
FIG. 10 is a back view of the cradle apparatus.

FIG. 10 is a back view of cradle apparatus 10. In FIG. 10, the components same as those of FIG. 1 are illustrated with the same reference numerals. As illustrated in FIG. 10, power connector 61 (third connector), USB connectors 62*a* and 62*b* (fourth connector), and screw hole 63 are provided in back portion 60 of cradle apparatus 10.

A connector of a power cable is connected to power connector 61. Power connector 61 is electrically connected by a wiring (via a wiring) with connector 14 provided in base portion 11. Accordingly, by connecting the power cable to power connector 61, power can be supplied to ultrasound diagnostic apparatus 20 mounted in cradle apparatus 10.

It is to be noted that, as described above, when ultrasound diagnostic apparatus 20 is mounted in cradle apparatus 10, power connector 42 of ultrasound diagnostic apparatus 20 is hidden by panel 17 such that the power cable is not connected. That is, when ultrasound diagnostic apparatus 20 is mounted in cradle apparatus 10, the power of the external power source is supplied to ultrasound diagnostic apparatus 20 only from cradle apparatus 10. That is, the power of the two external power sources is not supplied to ultrasound diagnostic apparatus 20.

A connector of a USB cable is connected to USB connectors 62*a* and 62*b*. USB connectors 62*a* and 62*b* are electrically connected by a wiring (via a wiring) with connector 14 provided in base portion 11. Accordingly, by connecting the USB cable connected with an external apparatus to USB connectors 62*a* and 62*b*, ultrasound diagnostic apparatus 20 mounted in cradle apparatus 10 can be communicated with the external apparatus. Examples of the external apparatus include a keyboard and a foot switch.

Screw hole 63 is a screw hole for fixing cradle apparatus 10 to cart 30, or a wall or a shelf of a hospital room, for example. Screw hole 63 is based on Video Electronics Standards Association (VASA) standard.

As described above, cradle apparatus 10 includes base portion 11 configured to support bottom portion 21 of ultrasound diagnostic apparatus 20, and back supporting portion 12 extending from base portion 11 along the attaching/detaching direction (z-axis direction) of ultrasound diagnostic apparatus 20 and configured to support back portion 25 on the side opposite to front portion 22 provided with display device 23 in ultrasound diagnostic apparatus 20. In addition, cradle apparatus 10 includes guides 13*aa*, 13*ab*, 13*ba* and 13*bb* provided in back supporting portion 12 and configured to be fitted with variable stand 43 (rail) provided in back portion 25 of ultrasound diagnostic apparatus 20 so as to allow ultrasound diagnostic apparatus 20 to slide along the attaching/detaching direction. With this configuration, cradle apparatus 10 can readily detachably support ultrasound diagnostic apparatus 20. For example, by setting variable stand 43 of ultrasound diagnostic apparatus 20 along guides 13*aa*, 13*ab*, 13*ba* and 13*bb* of cradle apparatus 10 and pushing ultrasound diagnostic apparatus 20 toward cradle apparatus 10, ultrasound diagnostic apparatus 20 can be readily mounted and supported in cradle apparatus 10. In addition, by pulling up ultrasound diagnostic apparatus 20 from cradle apparatus 10, cradle apparatus 10 can be readily dismounted.

In addition, since ultrasound diagnostic apparatus 20 can be readily attached to or detached from cradle apparatus 10, ultrasound diagnostic apparatus 20 is highly user-friendly. For example, when ultrasound diagnostic apparatus 20 is mounted in cradle apparatus 10, ultrasound diagnostic apparatus 20 can be used in a fixed manner. In addition, when ultrasound diagnostic apparatus 20 is dismounted from cradle apparatus 10, ultrasound diagnostic apparatus 20 can be used at various locations.

In addition, cradle apparatus 10 includes connector 14 configured to be connected with connector 51 provided in bottom portion 21 of ultrasound diagnostic apparatus 20. In addition, cradle apparatus 10 includes power connector 61 connected with connector 14 of base portion 11 in back portion 60. With this configuration, when a power cable is connected with power connector 61 of cradle apparatus 10, power can be supplied to ultrasound diagnostic apparatus 20 by only mounting ultrasound diagnostic apparatus 20 in cradle apparatus 10.

In addition, cradle apparatus 10 includes USB connectors 62*a* and 62*b* connected with connector 14 of base portion 11 in back portion 60. With this configuration, when USB connectors 62*a* and 62*b* of cradle apparatus 10 is connected with a USB cable connected with an external apparatus, communication with the external apparatus can be achieved by only mounting ultrasound diagnostic apparatus 20 in cradle apparatus 10. That is, it is not necessary to connect the USB cable to USB connectors 44*a* and 44*b* provided in back portion 25 of ultrasound diagnostic apparatus 20. In addition, when USB connectors 62*a* and 62*b* of cradle apparatus 10 are connected with an external apparatus connected with the USB cable, it is not necessary to pull out the USB cable from ultrasound diagnostic apparatus 20 when dismounting ultrasound diagnostic apparatus 20 from cradle apparatus 10.

In addition, cradle apparatus 10 includes panel 17 configured to hide power connector 42 such that the external power source is not connected to power connector 42 provided in back portion 25 of ultrasound diagnostic apparatus 20 when ultrasound diagnostic apparatus 20 is mounted in cradle apparatus 10. With this configuration, it is possible to prevent power of two external power sources from being supplied to ultrasound diagnostic apparatus 20, and thus malfunction of the apparatus can be reduced.

In addition, cradle apparatus 10 includes protrusion 15 protruding from back supporting portion 12, and configured to be fitted with recess 41 provided in back portion 25 of ultrasound diagnostic apparatus 20; and button 16 coupled with protrusion 15 and configured to pushed protrusion 15 into back supporting portion 12. With this configuration, cradle apparatus 10 can firmly fix ultrasound diagnostic apparatus 20.

It is to be noted that, the connector provided in back portion 60 of cradle apparatus 10 is not limited to a USB connector. Connectors of any other standards may also be adopted. In addition, a connector configured to be connected with the connector of the ultrasound probe may be provided in back portion 60 of cradle apparatus 10.

In addition, a plurality of connectors may be provided. In a case that a plurality of connectors are provided, ultrasound probes of multiple types may be connected to the cradle apparatus, for example. The operator of ultrasound diagnostic apparatus 20 can selectively use a desired ultrasound probe from among multiple types of ultrasound probes.

In addition, the numbers of connector 14 provided in base portion 11 of cradle apparatus 10 and USB connectors 62*a* and 62*b* provided in back portion 60 are not limited to the numbers of the above-mentioned embodiment.

In addition, the present invention is not limited to the above-mentioned configuration in which guides 13*aa*, 13*ab*, 13*ba* and 13*bb* are fitted with variable stand 43 of ultrasound diagnostic apparatus 20. For example, a rail configured to be slidably fitted with guides 13*aa*, 13*ab*, 13*ba* and 13*bb* may be provided separately from variable stand 43 in back portion 25 of ultrasound diagnostic apparatus 20.

In addition, guides 13*ab* and 13*bb* may be composed of a material which allows variable stand 43 to easily slide. With this configuration, ultrasound diagnostic apparatus 20 can smoothly slide when ultrasound diagnostic apparatus 20 is attached to or detached from cradle apparatus 10. Likewise, guides 13*aa* and 13*ba* may be composed of a material which allows variable stand 43 to easily slide.

Although embodiments of the present invention have been described and illustrated in detail, the disclosed embodiments are made for purpose of illustration and example only and not limitation. The scope of the present invention should be interpreted by terms of the appended claims.

What is claimed is:

1. A cradle apparatus configured to detachably support an ultrasound diagnostic apparatus, the cradle apparatus comprising:
a base configured to support a bottom of the ultrasound diagnostic apparatus when the ultrasound diagnostic apparatus is in a fully attached position on the cradle apparatus;
a back supporter extending from the base along an attaching/detaching direction of the ultrasound diagnostic apparatus, the back supporter being configured to support a back of the ultrasound diagnostic apparatus on a side opposite to a front of the ultrasound diagnostic apparatus when the ultrasound diagnostic apparatus is in a fully attached position on the cradle apparatus, the front being provided with a display device; and
a guide disposed in the back supporter, the guide including a first guide and a second guide facing each other with a space defined therebetween and configured to receive a rail provided in the back of the ultrasound diagnostic apparatus so as to allow the ultrasound diagnostic apparatus to slide along the attaching/detaching direction toward and away from the fully received position and to prevent the ultrasound diagnostic device from moving frontward and rearward from the fully attached position, wherein the rail is composed of a part of a stand provided in the back of the ultrasound diagnostic apparatus, the rail part of the stand being pivotable from a housed position against the back of the ultrasound diagnostic device to a raised position in which the stand is pivoted away from the back of the ultrasound diagnostic device to support the ultrasound diagnostic device in a standing state when the ultrasound diagnostic device is detached from the cradle apparatus, the cradle apparatus receiving and detachably supporting the ultrasound diagnostic apparatus when the rail part of the stand is in the housed position.

2. The cradle apparatus according to claim 1, wherein
a first connector is provided in the bottom of the ultrasound diagnostic apparatus; and
a second connector configured to be connected with the first connector is provided in the base.

3. The cradle apparatus according to claim 2, wherein
a third connector configured to be connected with an external power source is provided in the back supporter; and
the second connector is connected with the third connector via a wiring.

4. The cradle apparatus according to claim 2, wherein
a further connector configured to be connected with a signal line is provided in the back supporter; and
the second connector is connected with the further connector via a wiring.

5. The cradle apparatus according to claim 4, wherein a foot switch configured to control an operation of the ultrasound diagnostic apparatus is connected to the further connector.

6. The cradle apparatus according to claim 4, wherein an ultrasound probe is connected to the further connector.

7. The cradle apparatus according to claim 1, wherein a panel is provided in the back supporter, the panel being configured to hide a power connector such that, when the ultrasound diagnostic apparatus is mounted, an external power source is not connected to the power connector, the power connector being provided in the back of the ultrasound diagnostic apparatus.

8. The cradle apparatus according to claim 1, wherein
a protrusion is provided in the back supporter so as to protrude from the back supporter, the protrusion being configured to be fitted with a recess provided in the back of the ultrasound diagnostic apparatus; and
the protrusion is pushed into the back supporter when a button provided in the back supporter is pressed down.

9. The cradle apparatus according to claim 1, wherein the back supporter is fixed to a cart.

10. The cradle apparatus according to claim 1, wherein a further space is defined between the rail and a surface of the back of the ultrasound diagnostic apparatus, and one of the first guide and the second guide is received in the space when the ultrasound diagnostic device is in the fully received position.

11. A cradle apparatus in combination with an ultrasound diagnostic apparatus detachably supported by the cradle apparatus, the ultrasound diagnostic apparatus comprising a front with a display device, and a back on a side opposite the front surface, the back having a rail;

the cradle apparatus comprising:

a base configured to support a bottom of the ultrasound diagnostic apparatus when the ultrasound diagnostic apparatus is in a fully attached position on the cradle apparatus;

a back supporter extending from the base along an attaching/detaching direction of the ultrasound diagnostic apparatus, the back supporter being configured to support the back of the ultrasound diagnostic apparatus when the ultrasound diagnostic apparatus is in a fully attached position on the cradle apparatus; and a guide disposed in the back supporter, the guide including a first guide and a second guide facing each other with a space defined therebetween and configured to receive the rail provided in the back of the ultrasound diagnostic apparatus so as to allow the ultrasound diagnostic apparatus to slide along the attaching/detaching direction toward and away from the fully received position and to prevent the ultrasound diagnostic device from moving frontward and rearward from the fully attached position, wherein the rail is composed of a part of a stand provided in the back of the ultrasound diagnostic apparatus, the rail part of the stand being pivotable from a housed position against the back of the ultrasound diagnostic device to a raised position in which the stand is pivoted away from the back of the ultrasound diagnostic device to support the ultrasound diagnostic device in a standing state when the ultrasound diagnostic device is detached from the cradle apparatus, the cradle apparatus receiving and detachably supporting the ultrasound diagnostic apparatus when the rail part of the stand is in the housed position.

12. The cradle apparatus in combination with the ultrasound diagnostic apparatus as recited in claim 11, wherein a further space is defined between the rail and a surface of the back of the ultrasound diagnostic apparatus, and one of the first guide and the second guide is received in the space when the ultrasound diagnostic device is in the fully received position.

13. The cradle apparatus according to claim 1, wherein the guide is disposed rearward and above a portion of the base configured to support a bottom of the ultrasound diagnostic apparatus and between lateral sides of the ultrasound diagnostic apparatus when the ultrasound diagnostic apparatus is in the fully attached position.

\* \* \* \* \*